US005849281A

United States Patent [19]

Babinski et al.

[11] Patent Number: 5,849,281
[45] Date of Patent: Dec. 15, 1998

[54] METHOD OF SOAP-FREE SHAVING

[75] Inventors: Linda J. Babinski, Somers; James A. Limburg, Wind Point, both of Wis.

[73] Assignee: S. C. Johnson & Son, Inc., Racine, Wis.

[21] Appl. No.: 747,315

[22] Filed: Nov. 12, 1996

[51] Int. Cl.$^6$ ................................................. A61K 7/15
[52] U.S. Cl. ............................................................. 424/73
[58] Field of Search ................................................ 424/73

[56] References Cited

U.S. PATENT DOCUMENTS

| | | | |
|---|---|---|---|
| 654,740 | 7/1900 | Lease | 424/73 |
| 778,594 | 12/1904 | Megaro | 424/73 |
| 1,709,460 | 5/1929 | Caseau | 424/73 |
| 1,940,026 | 1/1933 | Smith | 424/73 |
| 3,429,964 | 2/1969 | Rieger | 424/73 |
| 3,541,581 | 11/1970 | Monson | 252/90 |
| 3,839,590 | 10/1974 | Battista | 424/359 |
| 3,852,417 | 12/1974 | McLaughlin | 424/47 |
| 4,046,874 | 9/1977 | Gabby et al. | 424/73 |
| 4,051,056 | 9/1977 | Hartman | 252/99 |
| 4,145,411 | 3/1979 | Mende | 424/45 |
| 4,155,870 | 5/1979 | Jorgensen | 252/131 |
| 4,157,387 | 6/1979 | Benedict | 424/54 |
| 4,187,288 | 2/1980 | Cordon et al. | 424/49 |
| 4,246,257 | 1/1981 | Elliot et al. | 424/78 |
| 4,252,694 | 2/1981 | Lewis et al. | 252/545 |
| 4,265,899 | 5/1981 | Lewis et al. | 424/270 |
| 4,381,293 | 4/1983 | Michel | 424/14 |
| 4,389,418 | 6/1983 | Burton | 424/365 |
| 4,421,769 | 12/1983 | Dixon et al. | 424/358 |
| 4,439,416 | 3/1984 | Cordon et al. | 424/47 |
| 4,451,482 | 5/1984 | Cagen | 424/284 |
| 4,497,825 | 2/1985 | Bade | 514/556 |
| 4,714,610 | 12/1987 | Gerstein | 424/70 |
| 4,735,746 | 4/1988 | Speranza et al. | 252/544 |
| 4,764,365 | 8/1988 | Boothe et al. | 424/81 |
| 4,786,432 | 11/1988 | Kanfer et al. | 252/120 |
| 4,847,071 | 7/1989 | Bissett et al. | 424/59 |
| 4,892,728 | 1/1990 | Kawa et al. | 424/70 |
| 4,892,729 | 1/1990 | Cavazza | 424/73 |
| 4,917,823 | 4/1990 | Maile, Jr. | 252/548 |
| 4,917,884 | 4/1990 | Roberts | 424/73 |
| 4,933,176 | 6/1990 | van Reeth | 424/70 |
| 4,957,732 | 9/1990 | Grollier et al. | 424/73 |
| 4,963,591 | 10/1990 | Fourman et al. | 514/944 |
| 4,970,220 | 11/1990 | Chaussee | 514/358 |
| 4,994,265 | 2/1991 | White | 424/73 |
| 4,999,183 | 3/1991 | Mackles et al. | 424/47 |
| 5,002,762 | 3/1991 | Bolich, Jr. | 424/70 |
| 5,034,220 | 7/1991 | Helioff et al. | 424/73 |
| 5,100,658 | 3/1992 | Bolich, Jr. et al. | 424/73 |
| 5,104,646 | 4/1992 | Bolich, Jr. et al. | 424/70 |
| 5,106,609 | 4/1992 | Bolich, Jr. et al. | 424/70 |
| 5,174,992 | 12/1992 | Lindauer et al. | 424/73 |
| 5,180,584 | 1/1993 | Sebag et al. | 424/401 |
| 5,234,619 | 8/1993 | Greene et al. | 252/108 |
| 5,234,689 | 8/1993 | Lindauer et al. | 424/401 |
| 5,262,154 | 11/1993 | Wendel et al. | 424/73 |
| 5,271,943 | 12/1993 | Bogart et al. | 424/484 |
| 5,290,471 | 3/1994 | Greene et al. | 252/108 |
| 5,294,438 | 3/1994 | Chang et al. | 424/73 |
| 5,298,181 | 3/1994 | Choy et al. | 252/95 |
| 5,326,556 | 7/1994 | Barnet et al. | 424/73 |
| 5,345,680 | 9/1994 | Vreeland et al. | 30/41 |
| 5,354,564 | 10/1994 | Borish et al. | 424/490 |
| 5,389,676 | 2/1995 | Michaels | 514/556 |
| 5,417,966 | 5/1995 | Futami | 424/73 |
| 5,420,118 | 5/1995 | Alban et al. | 514/63 |
| 5,451,396 | 9/1995 | Villars | 424/73 |
| 5,455,025 | 10/1995 | Pereira et al. | 424/59 |
| 5,520,908 | 5/1996 | Lundmark | 424/70.1 |
| 5,534,265 | 7/1996 | Fowler et al. | 424/489 |
| 5,556,628 | 9/1996 | Derian et al. | 424/401 |

OTHER PUBLICATIONS

K. Gallagher et al., 109 Cosmetics & Toiletries (12), 67–70 (1994).

*Primary Examiner*—Thurman K. Page
*Assistant Examiner*—James M. Spear

[57] ABSTRACT

Disclosed herein are highly rinsable shaving preparations that contain a behenylquaternary surfactant, a silicone and water. They are soap free, non-lathering, moisturizing shaving preparations. Preferred embodiments include plastic beads to assist in the removal of dead skin.

8 Claims, No Drawings

METHOD OF SOAP-FREE SHAVING

BACKGROUND OF THE INVENTION

The present invention relates to a method of shaving using a soap free, non-lathering shaving preparation. More particularly it relates to shaving preparations having exceptional moisturizing and skin softening capabilities without sacrificing rinsability.

"Soaps" are salts of fatty acids with various bases. Examples are the salts of fatty acids with ammonia, low molecular weight amines (especially alkanolamines) and alkali metals (especially sodium and potassium). Other fatty acid salts result from reaction with metallic cations (e.g. zinc and aluminum, alkaline earths such as calcium and magnesium), and long chain fatty amines. The most common soaps that are used in shaving preparations are stearates and palmitates.

However, soaps can cause irritation to the skin, particularly to delicate and broken skin during shaving. Soaps can also make rinsing more difficult, cause drying of the skin, and cause razor blades to prematurely dull.

Therefore, the art developed soap-free, non-lathering shave preparations. See e.g. U.S. Pat. No. 4,892,729. The disclosure of this patent and of all other publications referred to herein are incorporated by reference as if fully set forth herein. While prior art soap-free formulations solved certain problems, there was a desire to improve their moisturizing and skin softening properties. This presented a difficult challenge as many materials that moisturize or soften skin adversely affect rinsability.

In U.S. Pat. No. 4,389,418, moisturizing skin lotions were described which incorporated, among other things, mineral oil, certain quaternary ammonium surfactants, silicon oil, and isopropyl palmitate. However, these lotions were designed to be left on the skin. Thus, the patent did not address rinsability concerns. Similarly, Croda, Inc. proposed that behentrimonium methylsulfate $[CH_3(CH_2)_{21}-N(CH_3)_3]^+CH_3-SO_4^-$ be included in a skin lotion or a hair conditioner. See K. Gallagher et al., 109(12) Cosmetics & Toiletries 67–70 (1994).

A need exists for an improved shaving preparation which is of the non-soap type, which has superior moisturizing and skin softening properties, and which also has exceptional rinsability.

BRIEF SUMMARY OF THE INVENTION

In one aspect the invention provides a method of shaving by applying a shaving preparation comprising 0.1% to 30% by weight of a behenylquaternary surfactant, 0.1% to 30% by weight of an organo-substituted polysiloxane, and at least 10% by weight water to a surface to be shaved, and then shaving the surface with a razor.

In a preferred form there is at least 50% by weight water and the surfactant is a behentrimonium surfactant (e.g. behentrimonium methosulfate or behentrimonium chloride). Alternatively, the surfactant can be behenalkonium chloride or dibehenydimonium methosulfate or behenamidopropyl ethyldimonium ethosulfate.

Organo-substituted polysiloxanes, also known as silicones, are linear or cyclic polymers of monomeric silicon/oxygen monomers. The polymeric backbone of silicon is made up of alternating silicon and oxygen atoms. The silicon atoms may carry a wide variety of substituents which can be the same or different. Most often methyl and phenyl groups are used. However, other alkyl and aryl substitutes can be included. The most preferred silicone is dimethicone due to its superior blade protection properties.

In an especially preferred form the shaving preparation is essentially free of soap and is of the non-lathering type.

If desired, emollients can also be added. The preferred emollients are mineral oil and isopropyl palmitate. Various other emollients are also suitable such as petrolatum, fatty esters, fatty alcohols, glycerides, amino acids, lanolin, lanolin derivatives, plant derived oils, polyols and other silicone derivatives. The preferred range of emollients is 0.1% to 20% by weight.

To improve trackability (the ability of a consumer to see which areas have been shaved and which have not) it is desirable to also add a pigment (e.g. titanium dioxide). $TiO_2$ is preferably in the 0.01% to 5% range (by weight). Other known shaving preparation and skin lotion additives can also be included (e.g. vitamin E acetate USP, aloe vera powder, fragrances, other colorants, preservatives).

In a particularly preferred aspect, the shaving preparation also contains at least 0.01% by weight of plastic particles (e.g. beads). There can be a mixture of 9F polyethylene beads (from Allied Signal of Morristown, N.J.) having an average size of 100 microns with Acumist A45 beads (from Allied Signal of Morristown, N.J.), the latter being oxidized polyethylene beads of an average size of 45 microns. Various other plastics can be used such as those described in U.S. Pat. No. 5,534,265 or U.S. Ser. No. 08/634,602, filed Apr. 18, 1996 U.S. Pat. No. 5,587,156, by M. Wydowik. The addition of such plastics helps remove dead skin during shaving.

In another form, the invention provides a method of shaving a human skin surface having hair projecting therefrom. One applies the above shaving preparation to the surface and then shaves the surface with a razor.

It will be appreciated that notwithstanding that behenylquaternary surfactants are known to soften hair (as well as being good skin moisturizers), and that hair relaxants/softeners would normally be expected to interfere with good shaving (e.g. shavers often try to have hair "stand up" as it is being cut), the compositions of the present invention are able to achieve excellent shaving results while also achieving the superior skin softening and moisturizing results. Moreover, this is achieved with extremely good rinsability.

The objects of the present invention therefore include providing a shaving method which:

(a) does not use a soap;
(b) provides superior skin softening and moisturizing properties;
(c) is easy to rinse off; and
(d) has other desirable tracking and blade protection properties.

These and still other objects and advantages of the present invention (e.g. methods for using such shaving preparations) will be apparent from the description which follows. The description is merely of the preferred embodiments. The claims should be looked to in order to understand the full scope of the invention.

DETAILED DESCRIPTION

The preferred shaving preparations of the present invention contain the following ingredients:

| Ingredient | Weight Percentage Formula A | Weight Percentage Formula B |
| --- | --- | --- |
| dimethicone 200 | 8% | 8% |
| Incroquat Behenyl TMS-Croda, Inc. (behentrimonium methosulfate and cetearyl alcohol, 25% concentrate) | 5% | 5% |
| white mineral oil | 2% | 2% |
| isopropyl palmitate (30% strength) | 2% | 2% |
| titanium dioxide | 2% | 2% |
| Germaben II-E (diazolidinyl urea and parabens preservative) | 1% | 1% |
| Acumist A45 beads (oxidized polyethylene beads with average size of 45 microns) | 1.5% | 1.5% |
| 95 polyethylene beads (average size of 100 microns) | .5% | .5% |
| vitamin E acetate (tocopheryl acetate) | .1% | .1% |
| fragrance | .5% | .4% |
| aloe vera powder | — | .03% |
| water | 77.4% | 77.47% |
| various other dyes | remainder | remainder |

These shaving preparations were made using the following mixing process. We heated 70% of the water to 85° C., then added the behentrimonium methosulfate and mixed well. We then added mineral oil, silicone and isopropylpalmitate and mixed well. We then added titanium dioxide and mixed well. After that, we added the remaining water, mixed well, cooled to 100° F., added Germaben II-E, fragrance and vitamin E, mixed well, and then cooled to 85° F. with mixing. If used, the beads, dyes, and aloe vera can then be added.

We have also tested various other formulations, including formulations which substitute other behenylquaternary surfactants at the 5% level (e.g. behenalkonium chloride (Incroquat B 65C-Croda, Inc.) and dibehenydimonium methosulfate (Incroquat DBM-90-Croda, Inc.)).

Formulations were tested on human beings according to the following protocol. Each panelist was instructed to use the test product on their right leg for shaving. Panelists used their own brand of razor and shaved for one week (minimum 3 uses). They also followed this procedure with a standard shaving preparation for the left leg. Performance attributes of the product were rated. The testers reported that the formulations provided excellent moisturization and skin conditioning, good rinsability and retained other desired shaving preparation attributes.

Industrial Applicability

The present invention provides compounds useful as shaving preparations.

We claim:

1. A method of shaving, comprising:
    applying a shaving preparation, comprising:
        0.1% to 30% by weight of a behenylquaternary surfactant;
        0.1% to 30% by weight of a silicone; and
        at least 10% by weight of water to a surface to be shaved;
    then shaving the surface with a razor; and
    thereafter rinsing the shaved surface.

2. The method of claim 1, wherein the shaving preparation includes at least 50% by weight of water.

3. The method of claim 1, wherein the surfactant is a behentrimonium surfactant.

4. The method of claim 1, wherein the surfactant is selected from the group consisting of behentrimonium methosulfate, behenalkonium chloride, behentrimonium chloride, dibehenydimonium methosulfate and behenamidopropyl ethyldimonium ethosulfate.

5. The method of claim 1, wherein the shaving preparation further includes an emollient.

6. The method of claim 1, wherein the silicone is dimethicone.

7. A method of shaving, comprising:
    applying a shaving preparation, comprising:
        0.1% to 30% by weight of a behenylquaternary surfactant;
        at least 0.01% by weight of plastic particles;
        0.1% to 30% by weight of a silicone; and
        at least 10% by weight of water to a surface to be shaved; and
    then shaving the surface with a razor.

8. The method of claim 1, wherein the shaving preparation is a non-lathering shaving preparation.

* * * * *